United States Patent [19]
Matsui et al.

[11] Patent Number: 5,772,436
[45] Date of Patent: Jun. 30, 1998

[54] ODONTOTHERAPEUTIC HAND PIECE

[75] Inventors: Akira Matsui, 28-44, Tenjugaoka-cho, Hanazono, Ukyo-ku, Kyoto, 616; Fuminori Satoji, Yokkaichi; Yoshinori Morita, Hikone; Shigeo Kobayashi, Kuwana, all of Japan

[73] Assignees: Akira Matsui; J. Morita Manufacturing Corp., both of Kyoto; NTN Corporation, Osaka, all of Japan

[21] Appl. No.: 675,344

[22] Filed: Jul. 3, 1996

[30] Foreign Application Priority Data

Jul. 5, 1995 [JP] Japan .................................. 7-191031

[51] Int. Cl.⁶ .................................................. A61C 1/08
[52] U.S. Cl. ........................................ 433/126; 433/132
[58] Field of Search .................................... 433/132, 126, 433/114

[56] References Cited

U.S. PATENT DOCUMENTS

| | | |
|---|---|---|
| 1,653,212 | 12/1927 | Johnson et al. ........................ 433/126 |
| 2,090,885 | 8/1937 | Clark ...................................... 433/126 |
| 2,785,464 | 3/1957 | Hoffmeister ............................ 433/126 |
| 4,117,597 | 10/1978 | Trist et al. ............................. 433/132 |
| 4,941,828 | 7/1990 | Kimura ................................... 433/132 |
| 5,308,242 | 5/1994 | McLaughlin et al. ................... 433/126 |
| 5,374,189 | 12/1994 | Mendoza ................................. 433/132 |
| 5,554,026 | 9/1996 | Van Hale ................................ 433/132 |

*Primary Examiner*—Cary E. O'Connor
*Attorney, Agent, or Firm*—Koda & Androlia

[57] ABSTRACT

An odontotherapeutic hand piece is formed of a head portion, a handle portion connected to the head portion and a coupling portion arranged in continuation with the handle portion. A rotary member provided with turbine blades is accommodated in the head portion. The odontotherapeutic hand piece has a working medium conduit, which is arranged in an internal space of the coupling portion and is detachably engaged with the coupling portion for supplying a working medium to the odontotherapeutic hand piece. The head portion, the handle portion and the coupling portion are made of a material which permits integral molding. The head portion, the handle portion and the coupling portion are integrally joined together.

13 Claims, 12 Drawing Sheets

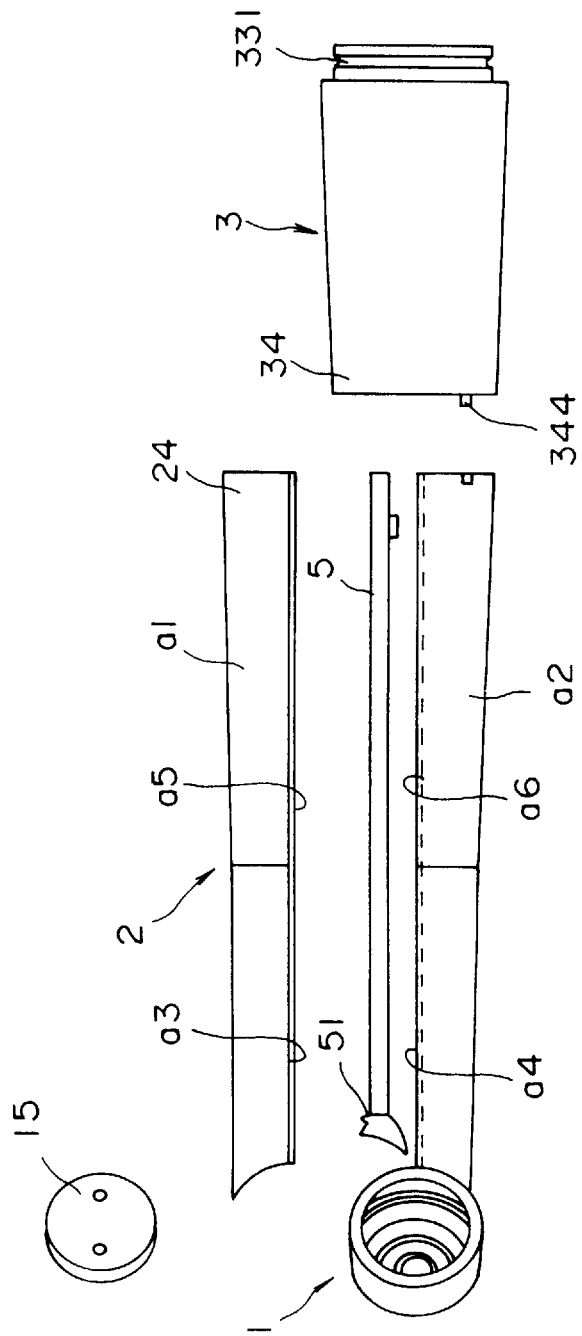

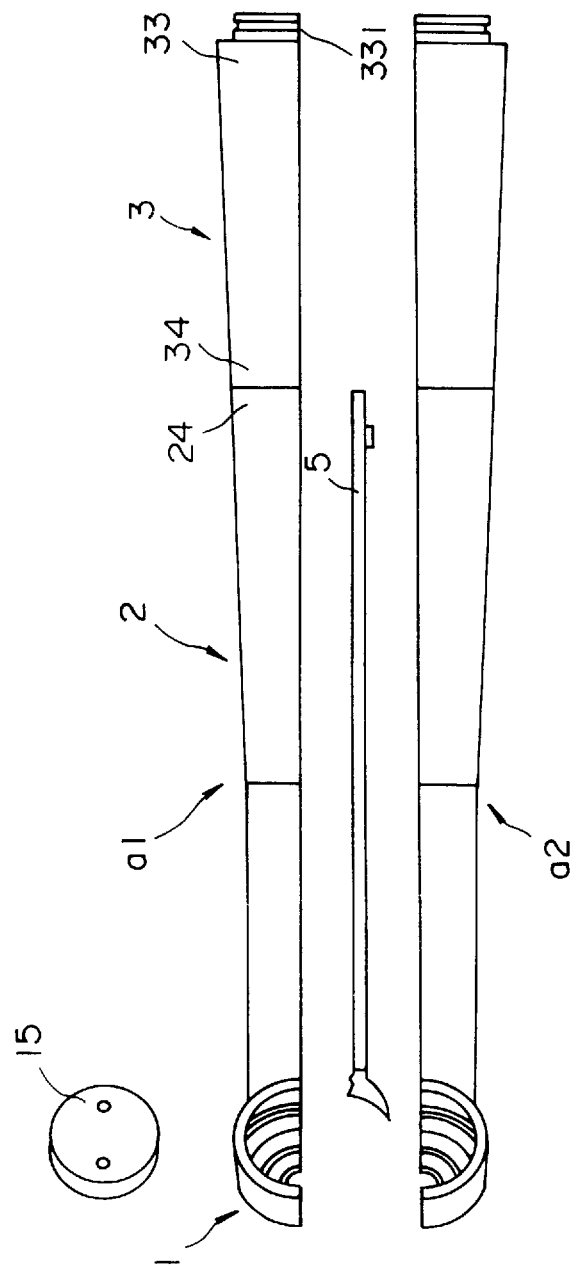

ODONTOTHERAPEUTIC HAND PIECE

FIELD OF THE INVENTION

This invention relates to an odontotherapeutic hand piece for use in dental treatments. Specifically, the present invention is concerned with an odontotherapeutic hand piece of the type that a tool, such as a cutting bar, arranged at a free end portion is rotated at a high speed by rotating drive force from a turbine, in other words, a so-called air turbine hand piece.

More specifically, this invention provides a high-performance and economical odontotherapeutic hand piece of the construction that a head portion in which a rotary member provided with turbine blades is accommodated, a handle portion and a coupling portion are arranged in continuation with each other and a working medium conduit is disposed in an internal space (i.e., an inner hollow portion) of the coupling portion and detachably engaged with the coupling portion to feed various working media (for example, pressurized air, pressurized water, a light guide for the illumination of a diseased part, etc.).

DESCRIPTION OF THE RELATED ART

A serious problem has recently arisen in the places of medical treatments, that is, an infectious pathogen such as human immunodeficiency virus or hepatitis virus is transferred from a patient to another via a medical instrument as a vehicle. The above problem also unexceptionally exists with respect to dental or surgical hand pieces for use in odontotherapy or surgical therapy (hereinafter called "odontotherapeutic hand pieces" or simply "hand pieces").

The above-described problem is caused by repeated use of an odontotherapeutic hand piece. To cut off a route of infection of an infectious pathogen, two methods may be contemplated, one being to completely sterilize each hand piece and the other to use a fresh hand piece for each patient.

However, the above-described sterilization method is not considered to be perfect. On the other hand, use of a fresh hand piece for each patient forces the patient to bear a high medical cost because a conventional hand piece is high in cost.

With a view to coping with this problem, a variety of hand pieces which are thrown away after being used for individual patients, that is, of the disposable type have been proposed recently. These disposable hand pieces are however accompanied by the problem that they cannot permit complete and sufficient dental treatments because due to placement of too much importance on economy, they are inherently inferior in performance or they are lowered in performance or they become unusable during treatments due to placement of too much importance on economy.

For example, most of conventional disposable odontotherapeutic hand pieces made of a synthetic resin (plastic) have only a single function, for example, due to unreplaceability of a cutting bar arranged at free end portions and moreover, are extremely inferior in performance and function to conventionally-employed general-purpose products.

It has therefore been necessary to provide plural types (for example, plural tool types) of disposable hand pieces in each therapeutic activity for each patient and to selectively use them as needed. Even though the hand pieces are inexpensive when taken individually, it is the current situation that no cost reduction can be achieved because plural hand pieces are used.

Further, such conventional disposable odontotherapeutic hand pieces made of a synthetic resin involve problems in function and performance due to their low working or molding accuracy compared with the conventional non-disposable ones, specifically, metal-made odontotherapeutic hand pieces which are manufactured by precise machining or the like, thereby still keeping such conventional disposable hand pieces made of a synthetic resin for replacing expensive hand pieces which have been commonly used to date. In other words, it is the current situation that from the viewpoint of the safety of therapeutic activities and the like, a conventional metal-made expensive odontotherapeutic hand piece is repeatedly used for a number of patients by sterilizing it after dental treatment of each patient.

SUMMARY OF THE INVENTION

An object of the present invention is to overcome the above-described problems of the conventional art and to provide an odontotherapeutic hand piece comparable in performance and function with metal-made hand pieces, which are manufactured by conventional precision machining, and excellent in cost merit (economy) no matter whether the hand piece is of the recycling type or of the disposable type.

In one aspect of the present invention, there is thus provided an odontotherapeutic hand piece formed of a head portion, in which a rotary member provided with turbine blades is accommodated, a handle portion connected to said head portion and a coupling portion arranged in continuation with said handle portion, said odontotherapeutic hand piece having a working medium conduit arranged in an internal space of said coupling portion and detachably engaged with said coupling portion for supplying a working medium to said odontotherapeutic hand piece, wherein:

(i) said head portion, said handle portion and said coupling portion are made of a material which permits integral molding; and (ii) said head portion, said handle portion and said coupling portion are integrally joined together.

In another aspect of the present invention, there is also provided a process for the production of an odontotherapeutic hand piece formed of a head portion, in which a rotary member provided with turbine blades is accommodated, a handle portion connected to said head portion and a coupling portion arranged in continuation with said handle portion, said odontotherapeutic hand piece having a working medium conduit arranged in an internal space of said coupling portion and detachably engaged with said coupling portion for supplying a working medium to said odontotherapeutic hand piece, wherein said process comprises:

(i) molding said head portion, said handle portion and said coupling portion as discrete members or molding two of said head portion, said handle portion and said coupling portion as an integral member and the remaining portion as a discrete member, all with a synthetic resin, whereby plural split members are formed; and (ii) integrally bonding said split members together.

In the odontotherapeutic hand piece according to the present invention, the head portion, handle portion and coupling portion as principal elements of the hand piece are constructed based on plural split members each of which has been integrally formed from a material permitting integral molding, for example, by injection molding or the like of a synthetic resin, and the split members have been joined together by welding to the like. In particular, the use of such a synthetic resin as the material permitting integral molding makes it possible to provide the split members with an accuracy of a degree similar to that available from the conventional precision machining.

Compared with conventional metal-made hand pieces manufactured by precise machining, the individual elements can be provided with comparable accuracy, permit far easier, less time-consuming molding and assembly work, and make it possible to substantially reduce the manufacturing cost and hence the price.

The above-described advantages have important significance in view of the strong demand for a high-performance and economical disposable hand piece as a reflex of the recent viral infectious disease, AIDS and like problems.

The above-described high-performance hand piece can be realized by the adoption of novel air supply/exhaust system, working medium supply system and illuminating optical system which are applied to the odontotherapeutic hand piece according to the present invention. These systems can be readily fabricated with a material which permits integral molding, for example, with a synthetic resin, and can be optimized by adopting a shielding plate which is arranged inside a main body (i.e., head main body formed of the head portion, the handle portion and the coupling portion) of the hand piece.

In view of the recent move toward formation of the working medium conduit as a unit, the construction of the coupling portion in the odontotherapeutic hand piece according to the present invention conforms with the construction of the unit-type working medium conduit. The odontotherapeutic hand piece according to the present invention has been developed based on the finding that the construction of such a coupling portion can be accomplished by integral molding of a material which permits integral molding.

The odontotherapeutic hand piece according to the present invention can be connected to conventional working medium conduits which are unit-type products, and has replaceability with conventional hand pieces and hence wide applicability.

Moreover, use of a synthetic resin as a material permitting integral molding in the present invention can realize an odontotherapeutic hand piece of lightweight construction, thereby permitting easier handling by a user such as a dentist. Where the individual split members are made of a synthetic resin, ultrasonic welding can be adopted as a method for bonding them together. This makes it possible to achieve complete integral bonding irrespective of the kind of the synthetic resin. Especially, even if the synthetic resin is a high-function material called "high-engineering plastics", fail-free bonding is possible by ultrasonic welding so that an odontotherapeutic hand piece of a still higher additional value can be furnished by the present invention.

BRIEF DESCRIPTION OF THE DRAWINGS

FIG. 11 is a plan view of split members which make up an odontotherapeutic hand piece according to a second embodiment of the present invention;

FIG. 12 is a plan view of split members which make up an odontotherapeutic hand piece according to a third embodiment of the present invention;

DETAILED DESCRIPTION OF THE INVENTION AND PREFERRED EMBODIMENTS

Figure 1:
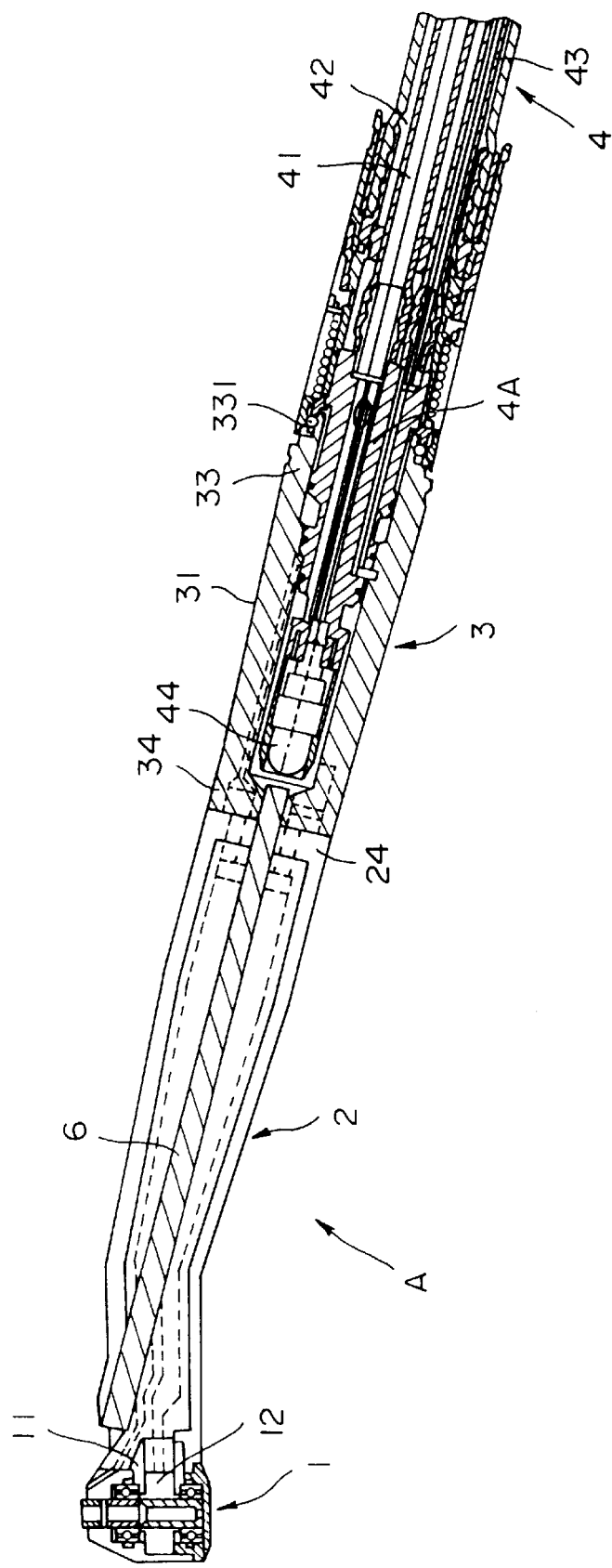
FIG. 1 is a cross-sectional view of an odontotherapeutic hand piece according to a first embodiment of the present invention.

The technical features and preferred embodiments of the present invention will hereinafter be described in detail with reference to the accompanying drawings.

Needless to say, it should be borne in mind that the present invention is not limited to or by the embodiments illustrated in the drawings.

The odontotherapeutic hand piece according to the present invention is produced typically by a synthetic resin (plastics) as described above. A description will first be made about the motive for the formation the odontotherapeutic hand piece with a synthetic resin by the present inventors.

The direct motive for the development of the resin-made odontotherapeutic hand piece according to the present invention goes back to the development of a hand piece by the present inventors, in which a new air supply/exhaust system was assembled with a view to improving the performance of conventional expensive metal-made odontotherapeutic hand pieces.

A small fluid-driven turbine hand piece with the above-described new air supply/exhaust system assembled therein has already been proposed by the present inventors (see, for example, U.S. patent application Ser. No. 08/381,508).

The small fluid-driven turbine hand piece previously proposed by the present inventors features a new construction which supplies compressed air to and exhausts it from a rotary member of a head portion.

More specifically, the small fluid-driven turbine hand piece previously proposed by the present inventors is equipped with a new air supply/exhaust system which comprises a single air inlet for supplying compressed air against the rotary member arranged inside the head portion and one or more air outlets arranged at place(s) extremely close to the single air inlet.

For example, the air supply/exhaust system comprises the above-mentioned single air inlet and two air outlets arranged at places which are extremely close to the single air inlet and are located above and below the single air inlet, respectively. The new air supply/exhaust previously proposed by the present inventors is of a simple construction at first glance but is quite different in nature from the conventional art. Owing to its construction, surprisingly high performance has been achieved, because in the new air supply/exhaust system of the odontotherapeutic hand piece previously proposed by the present inventors, compressed air supplied into a head chamber presents a flow completely different from any flow available by the conventional art.

Namely, in the above-described small fluid-driven turbine hand piece previously proposed by the present inventors, a flow of compressed air supplied into the head chamber collides against a turbine blade and without whirling in the chamber, is immediately exhausted through the air outlets arranged at the places closed to the air inlet.

In each conventional air supply/exhaust system, on the other hand, a flow of compressed air whirls inside a chamber subsequent to its collision against a turbine blade, and the flow of compressed air is then exhausted through an air outlet arranged at the position of an end of the whirl.

A totally unexpected difference is obtained between the two air supply/exhaust systems (i.e., the non-whirling system and the whirling system). Described specifically, the conventional system (the whirling system) is on the order of 200,000 to 350,00 rpm in the revolution speed of a tool while the new system (the non-whirling system) previously proposed the present inventors has been improved to the order of 500,000 rpm, thereby making it possible to produce a high torque.

The above-described difference in performance between both the systems is theoretically discussed in detail in the above-mentioned patent application. The low performance by the conventional system (the whirling system) is primarily attributed to the fact that the flow of compressed air, which swirls inside the chamber, acts as a large resistor.

In the course of the development of the small fluid-driven turbine hand piece previously proposed by the present inventors, an idea was developed, that is, to form the head portion with plastics.

Since the flow of compressed air blown into the chamber of the head portion is immediately exhausted from the system, the following matters came to the knowledge:

no large load is applied to the chamber of the head portion, and no large load is applied to a cap portion which covers the chamber of the head portion.

This knowledge then led to the following findings:

a housing and the cap portion of the head portion can be constructed in a simple detachable form, and because the air inlet and outlet(s) for supplying compressed air into the chamber of the head portion and exhausting it from the chamber can be arranged close to each other as mentioned above, the above-described air supply/exhaust system can be constructed making effective use of a shielding plate which is used to form a passage for working medium within the handle portion of the hand piece.

These knowledge and findings served together as a basis for the present invention.

The present invention has been developed under the above-described background, and can provide an odontotherapeutic hand piece made of a material permitting integral molding, such as a synthetic resin, and having excellent properties and functions capable of overcoming the above-mentioned problems and also meeting the above-mentioned various requirements.

Referring first to FIG. 1 to FIG. 8, the odontotherapeutic hand piece according to the first embodiment of the present invention will be described.

Figure 2:
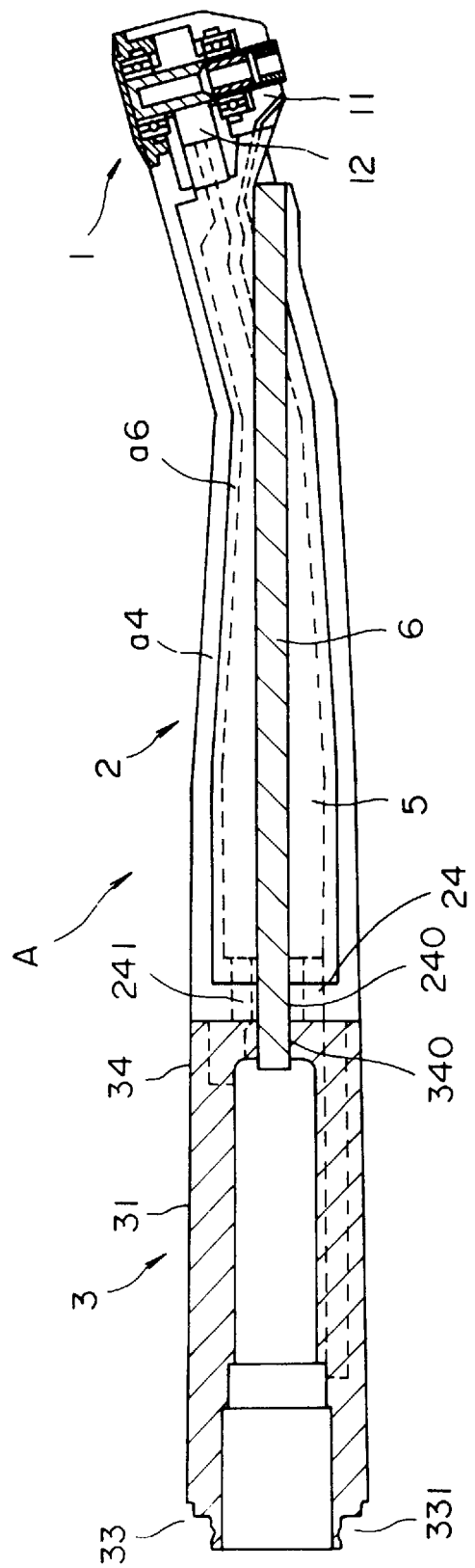
FIG. 2 is a fragmentary cross-sectional view of the odontotherapeutic hand piece according to the first embodiment of the present invention (other than a working medium conduit)
Figure 3:
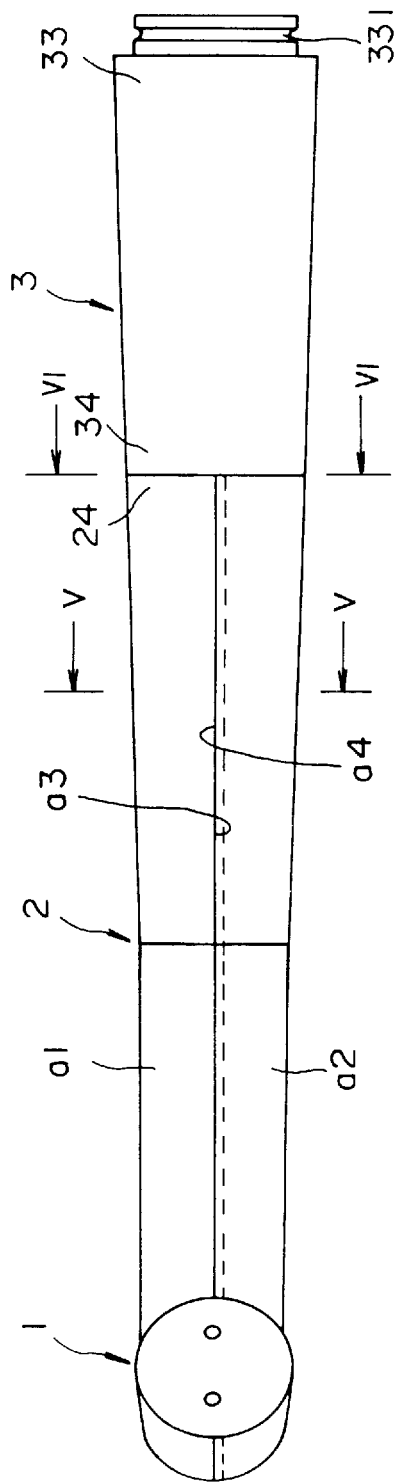
FIG. 3 is a plan view of the odontotherapeutic hand piece according to the first embodiment of the present invention (other than the working medium conduit)

As is shown in FIG. 1 to FIG. 3, the odontotherapeutic hand piece according to the first embodiment of the present invention, which is generally designated by letter A, is formed of the following principal elements:

i) a head portion 1 in which a rotary member 11 equipped with turbine blades 12 is accommodated, ii) a hand portion 2 arranged in continuation with the head portion 1, iii) a coupling portion 3 arranged in continuation with the handle portion 2, and iv) a working medium conduit 4 arranged in an internal space of the coupling portion 3 and detachably engaged with the coupling portion 3 for supplying various working media to the odontotherapeutic hand piece.

The basic internal construction of the odontotherapeutic hand piece A according to the present invention is similar to those of the conventional general hand pieces.

In the odontotherapeutic hand piece depicted in FIG. 1, there are shown working medium passages for compressed air adapted to drive the turbine blades 12, compressed water for cooling a place under treatment and the like and also a light guide for illuminating a diseased surface or part.

Descried more specifically, the odontotherapeutic hand piece A shown in FIG. 1 is provided with working medium passages (pipes, ducts), which comprise an air supply pipe 41, an air exhaust pipe 42 and a water supply pipe 43, and also with a straight or linear light guide 6 arranged in the handle portion 2 for the illumination of a diseased surface or part.

It is to be noted that for the sake of simplification, an electric power supply duct for supplying electric power to a light source 44 of the light guide 6, said electric power supply duct being also one of the passages for working media, is omitted in FIG. 1.

In the present invention, the working medium passages, needless to say, may comprise a cooling air pipe for cooling a place under treatment or an air pipe arranged in combination with an air supply pipe to permit supplying water in the form of a spray.

As is illustrated in FIG. 1, the various working medium passages (pipes, ducts) are collectively called the "working medium conduit 4" in the odontotherapeutic hand piece A according to the present invention.

Further, the above-described working medium conduit 4, which is adopted in the odontotherapeutic hand piece A according to the first embodiment of the present invention, is of the construction that the working medium conduit 4 is inserted into the coupling portion 3 through a rear end of the coupling portion and is detachably locked there.

As will be described subsequently herein, the working medium conduit 4 is of the construction that it is detachably locked and fixed with the coupling portion 3. When locked with the coupling portion 3, the working medium conduit 4 cooperates with the internal construction of the coupling portion 3 so that the passages for various function media are communicated with their corresponding working medium passages arranged inside the handle portion 2, thereby exhibiting functions to supply the various function media to required places and to exhaust them from such places.

Incidentally, into the light guide 6 arranged inside the handle portion 2, illuminating light is emitted from the light source 44 of the working medium conduit 4.

In the present invention, the light guide 6 is made of a light-conductive material. The light guide shown in the drawing is formed of a straight (linear) glass rod from the viewpoint of economy.

Incidentally, usable examples of the above-described light-conductive material include a bundle of glass fibers (i.e., a glass fiber cable), a bundle of plastic fibers (i.e., a plastic fiber cable), and a glass rod with a reflective film coated therearound.

As is shown in FIG. 1, the glass rod as the light guide 6 is in a straight form and is arranged with a space left around it. In this case, between the refractive index of the glass rod and the refractive index of the space (air), the later refractive index is smaller so that a structure identical to a clad glass fiber of the total reflection type has been accomplished. It is therefore possible to provide an excellent optical transmission system having an extremely small attenuation rate in optical transmission.

In the odontotherapeutic hand piece A according to the first embodiment of the present invention, a first significant feature resides in that the head portion 1, the handle portion 2 and the coupling portion 3 are each made of a material which permits integral molding.

Namely, the odontotherapeutic hand piece A according to the present invention is constructed of plural split members (elements) made of the material permitting integral molding, and these split members are integrally joined together.

Usable examples of the material permitting integral molding include injection-molding synthetic resins and die-casting aluminum alloys.

As the injection-molding synthetic resin, one having heat resistance (for example, 135° C., 2.5 kfg/cm$^2$, 10–15 minutes) and chemical resistance is preferred because odontotherapeutic hand pieces of this type are subjected to sterilization in an autoclave. Usable examples include polyether imides (PEIs), polyether sulfones (PESs), polyether ketones and polyimides. These synthetic resins are desired to have heat resistance of at least 100° C. in terms of glass transition point. Polyether imides typically have a glass transition point of 217° C., polyether sulfones typically have a glass transition point of 225° C., polyether ketones typically have a glass transition point of 175 v, and polyimides typically have a glass transition point of 250° C. Each of these resins does not undergo deformation up to the temperature of its glass transition point and permits injection molding. An odontotherapeutic hand piece made of such a resin retains durability even when repeatedly subjected to sterilization in an autoclave. Such a resin can therefore provide an odontotherapeutic hand piece, which can be used semi-permanently like conventional metal-made hand pieces rather than in a disposable fashion and can be produced at low cost. Among the above-exemplified resins having heat and chemical resistance, polyether imides (PEIs) are most preferred because they do not develop microcracks even when repeatedly subjected to sterilization in an autoclave.

Further, those composed of such synthetic resins and antibacterial agents are also preferred materials. For example, a polyether sulfone (PES) added with 5–20 wt. % of fine titanium oxide particles or 0.5–1.0 wt. % of silver-deposited hydroxyapatite as an antibacterial agent is used. As the above-mentioned antibacterial agent, it is possible to use, besides the above-mentioned silver-deposited hydroxyapatite, silver-copper zeolite, silver phosphate zirconium, silver phosphate glass, silver phosphate ceramic, silver titania or the like.

In the present invention, the above-described joining between the split members can be effected using a desired joining method capable of providing a firm connection, such as adhesion, bonding or welding. For example, where the split members are made of a synthetic resin, it is possible to adopt ultrasonic welding, solvent welding in which the split members are dissolved at bonding surfaces with dichloromethane (methylene chloride) or the like and are bonded together, thermal welding, laser welding or the like.

Among the above-exemplified joining methods, ultrasonic welding is extremely useful for small hand pieces of this type because this joining method can weld not only contacting parts lying in the direction of application of an ultrasonic wave but also contacting parts lying in a direction perpendicular to the direction of application of the ultrasonic wave. This finding is not known to the public but has been confirmed by the present inventors.

Upon ultrasonic welding, it is preferred to integrally form joining ribs on joining surfaces of split members in advance.

FIG. 4 to FIG. 8 illustrate certain characteristic features of the odontotherapeutic hand piece A according to the first embodiment of the present invention.

In the illustrated embodiment, constituting members of the hand piece A comprise a split member a which is an integrated combination of the head portion 1 and the handle portion 2 and is formed of a pair of left-hand and right-hand, half-split members a1,a2. Included as other constituting members are a shielding plate 5 arranged as a partition between the paired left-hand and right-hand, half-split members a1,a2 and the coupling portion 3 integrally molded with a synthetic resin and having a construction shown in FIGS. 10(a) to 10(c) to be described subsequently herein.

The split member a as a constituting member of the head portion 1 and the handle portion 2, that is, the paired left-hand and right-hand, split members a1,a2 are each in the form of a gutter having a substantially semi-circular cross-section.

Bonding surfaces a3,a4 of the paired left-hand and right-hand, half-split members a1,a2 are formed so that they are coplanar with a rotary shaft 13 (see FIG. 13) of the rotary member accommodated within the chamber (space) of the head portion 1.

Further, the bonding surfaces a3,a4 are provided with convexities a5 and concavities a6, respectively, for the sake of convenience for positioning upon bonding.

In the illustrated embodiment, a rib a7 is formed on an inner peripheral wall of the left-hand half-split member a2 for the formation of passages for working media. Needless to say, the bonding of the bonding surfaces a3,a4 of the paired left-hand and right-hand, split members a1,a2 can be conducted with the shielding plate 5 interposed therebetween in the present invention.

Figure 5:
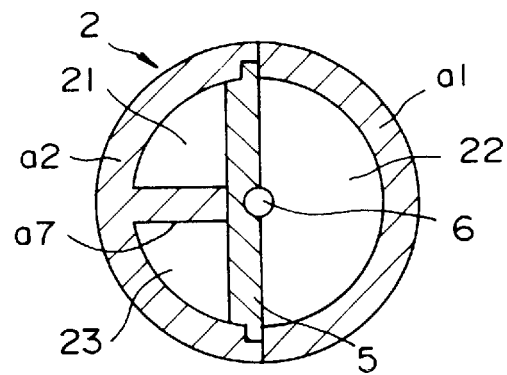
FIG. 5 is a cross-sectional view taken in the direction of arrows V—V of FIG. 3.

The rib a7 is, as shown in FIG. 5, in contact with a left-hand side of the shielding plate 5, whereby an internal space of the left-hand half-split member a2 is divided into two sections. Incidentally, these divided sections are used as working medium passages, that is, as an air supply passage 21 and a water supply passage 23. On the other hand, an internal space of the right-hand half-split member a1 is used as the light guide 6 and an air exhaust passage 22.

The convexities a5, concavities a6 and rib a7 can be provided with a function as ribs for ultrasonic welding. Namely, when ultrasonic welding is applied at the places of the convexities a5, concavities a6 an rib a7, the split member a and the shielding plate 5 are welded together at contacting parts thereof.

The shielding plate 5 is preferably provided with a groove for holding the light guide 6 so that the light guide 6 is stably held in place. Details of the shielding plate 5 will be described subsequently herein.

As is shown in FIG. 2, the handle portion 2 and the coupling portion 3 are provided at contacting end faces thereof with sealing end portions 24,34, respectively.

As is illustrated in the drawings, the sealing end portions 24,34 are provided communication holes 241,341 and light guide holding holes 240,340 for holding the light guide 6 at the position of a central axis of the handle portion 2.

In the above-described odontotherapeutic hand piece A according to the first embodiment of the present invention, the head portion 1 is formed together with the handle portion 2 as a split structure which is formed of the paired left-hand and right-hand, half-split members as described above (see FIG. 4).

Corresponding to the above-described split structure, the rotary member 11 is integrally assembled inside the head portion.

Figure 7:
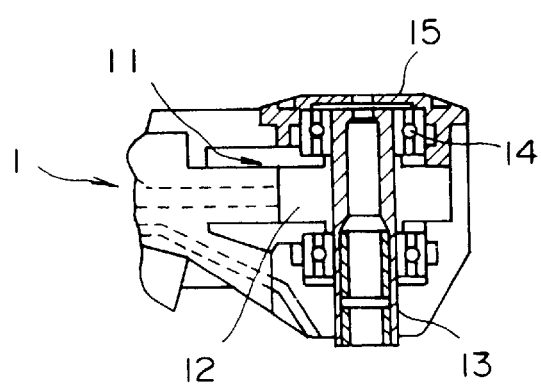
FIG. 7 is a cross-sectional view of a head portion of the odontotherapeutic hand piece according to the first embodiment of the present invention.

In the head portion 1, the rotary member 11 is primarily composed, as shown in FIG. 7, of the rotary shaft 13 arranged in a cylindrical chamber of the head 1 for detachable attachment of one of various tools such as a cutting bar and turbine blades 12 integrally arranged on the rotary shaft 13. The rotary member 11 may be formed of plastics except for the rotary shaft 13.

A bearing 14 which rotatably supports the rotary shaft 13 thereon is a metal-made ball bearing in the case of the illustrated embodiment. Pneumatic bearing permitting rotation at a still higher revolution speed may also be adopted.

Figure 6:
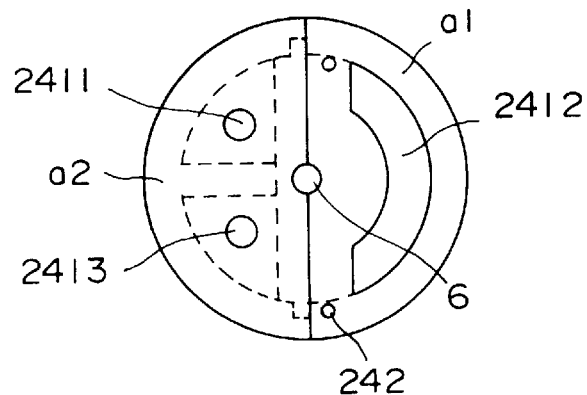
FIG. 6 is a cross-sectional view taken in the direction of arrows VI—VI of FIG. 3.

The outline construction of the shielding plate 5 applicable to the odontotherapeutic hand piece A according to the first embodiment of the present invention has been described with reference to FIG. 4 to FIG. 6. Here, the details of the construction of the shielding plate 5 will be described with reference to FIG. 8 to FIG. 9.

Figure 4:
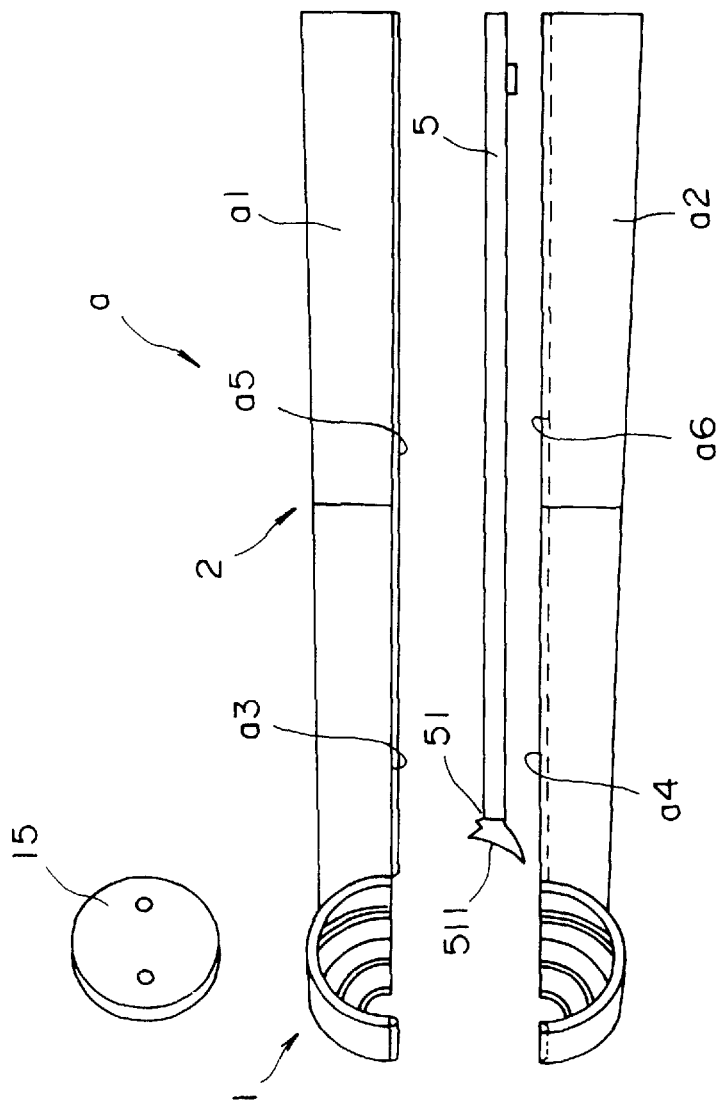
FIG. 4 is a plan view of split members which make up the odontotherapeutic hand piece according to the first embodiment of the present invention.
Figure 8:
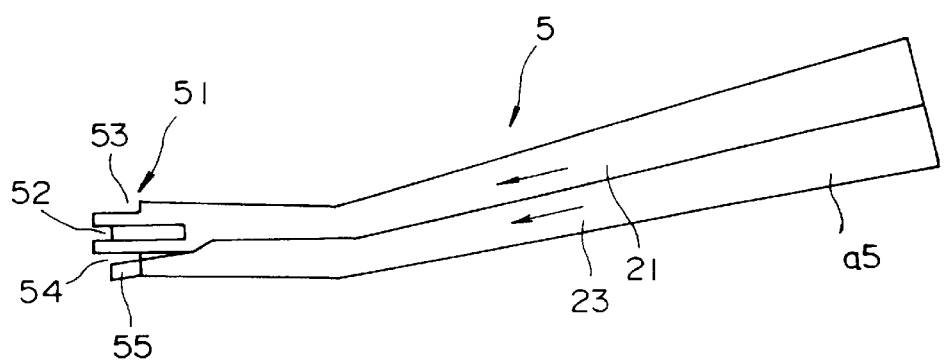
FIG. 8 is a left-hand side view of a shielding plate applied to the odontotherapeutic hand piece according to the first embodiment of the present invention.

FIG. 8 is the left-hand side view of the shielding plate 5, namely, is a side view of the side 5a facing the left-hand half-split member a2 (see FIG. 4). On the other hand, FIG. 9 is the right-hand side view of the shielding plate 5, that is, a side view of a side 5b facing the right-hand half-split member a1.

As is depicted in FIG. 4 which shows the shielding plate 5 in plan, a spherical portion 511 of a free end portion (located on the side of the head portion) 51 of the shielding plate 5 constitutes a part of a wall of the cylindrical chamber of the head portion 1.

Figure 9:
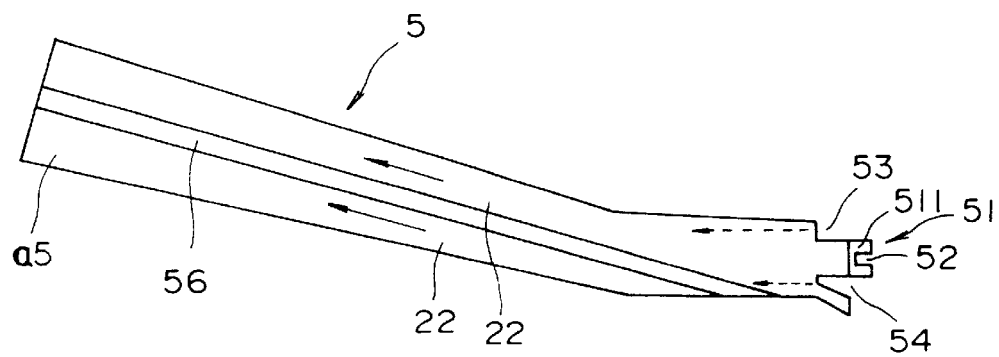
FIG. 9 is a right-hand side view of a shielding plate applied to the odontotherapeutic hand piece according to the first embodiment of the present invention.

The construction of the above-described free end portion 51 of the shielding plate 5 is illustrated in FIG. 8 to FIG. 9.

As is shown in these drawings, the free end portion 51 of the shielding plate 5 is provided with a single air inlet 52 and two air outlets 53,54 arranged at places close to the air inlet 52 and located above and below the air inlet 52, respectively, and is also provided with a water-supplying guide portion 55.

Needless to say, the air inlet 52 is formed in communication with the air supply passage 21 and the water-supplying guide portion 55 is formed in communication with the water supply passage 23. Further, the two air outlets 53,54 are obviously arranged in communication with the air exhaust passage 22 as is shown in FIG. 9.

The above-described air supply/exhaust system is the new air supply/exhaust system adopted in the small high-performance odontotherapeutic hand piece previously proposed by the present inventors in U.S. patent application Ser. No. 08/381,508. The characteristic feature of the air supply/exhaust system resides in that the air outlet(s) is(are) arranged close to an air inlet and in the illustrated embodiment, resides in that the two air outlets 53,54 are arranged close to the single air inlet 52 and at locations above and below the single air inlet 52. This feature is totally different from the conventional art.

Incidentally, the above-described air inlet/exhaust system can be achieved with extreme ease by the adoption of the above-described shielding plate 5 which is useful in the present invention.

Further, FIG. 9 also shows another significant characteristic feature of the odontotherapeutic hand piece A according to the first embodiment.

FIG. 1 to FIG. 2 illustrate an embodiment for guiding the light guide 6 linearly to an emitting opening of illuminating light. FIG. 9 shows that the shielding plate 5 is formed of one having a light-guide-holding groove 56 for linearly guiding the light guide 6.

In the holding structure for the light guide 6 by the light-guide-holding groove 56 of the shielding plate 5, the light guide 6 is arranged in the holding groove 56 and is fixed at opposite ends thereof. The light guide 6 is therefore exposed to air (air to be exhausted) at an outer peripheral wall thereof other than the fixed ends thereof. This holding structure for the light guide 6 has important significance as will be described hereinbelow.

In general, the light guide 6 applied to the illumination system can be formed of one of various examples. In the illustrated embodiment, the light guide 6 is formed of a single straight glass rod.

In the holding structure for the light guide 6 in the above-described illumination system according to the present invention, the refractive index of glass is greater than that of surrounding air so that the optical transmission system composed of the light guide 6 is the same as a clad glass fiber system. It is therefore possible to prevent attenuation of illuminating light. The clad glass fiber system is to make the refractive index of the core of each glass fiber different from that of its clad so that total reflection of light under transmission is achieved to avoid attenuation of the light under transmission.

The holding structure for the light guide 6 can be easily accomplished by the structure of the shielding plate 5.

Figure 10A:
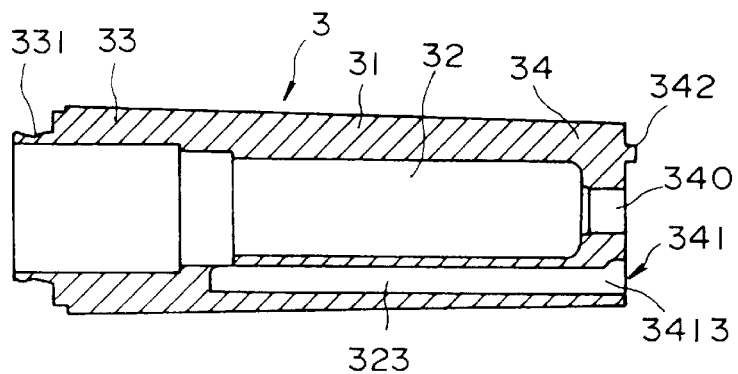
FIGS. 10A, 10B and 10C illustrate the construction of a coupling portion applied to the odontotherapeutic hand piece according to the first embodiment of the present invention.
Figure 10B:
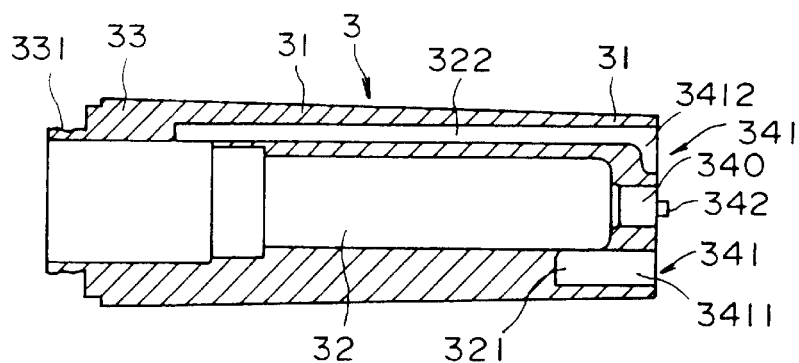
Figure 10C:
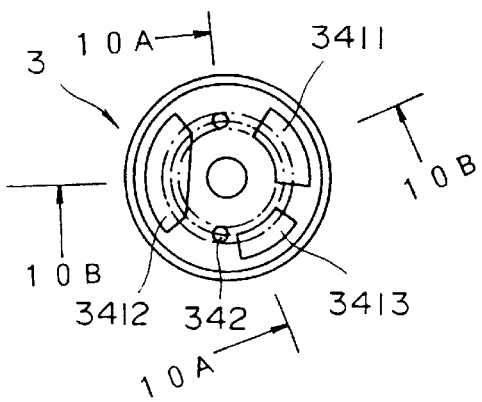

FIGS. 10A, 10B and 10C illustrate the construction of the coupling portion 3 applied to the odontotherapeutic hand piece according to the first embodiment of the present invention.

The coupling portion 3 in the present invention is formed of an integrally molded product which has been produced, for example, by injection molding a synthetic resin. The coupling portion 3 comprises:

i) the sealing end portion 34 defining a communication hole 341 which is communicated and connected with the working medium passage arranged inside the handle portion 2, ii) a main body portion 31 defining a communication hole 32 receiving therein a free end portion (the portion shown at 4A in FIG. 1 and forming a coupling portion on a side of the working medium conduit) of the working medium conduit 4 (not shown) and cooperating with the working medium conduit 4 in a manner to be described subsequently herein so that the working medium conduit is formed, and iii) an engaging portion 33 detachably engageable with an engaging portion of the working medium conduit 33.

The sealing end portion 34 of the coupling portion 3 forms a portion bonded with the sealing end portion 24 of the handle portion 2. The sealing end portion 34 of the coupling portion 3 is provided with three communication holes 341 (3411 to 3413) in correspondence to three communication holes 241 (2411 to 2413) in the sealing end portion 24, said three communication holes 241 being in communication with the air supply passage 21, air exhaust passage 22 and water supply passage 23 formed as working medium passages in the handle portion 2.

FIG. 10 to FIG. 10C show, as the communication holes 341, holes formed in communication with the air supply passage 321, the air exhaust passage 322 and the water supply passage 323. Further, the holding hole 340 for holding the light guide 6 at a central part of the sealing end portion 34 is illustrated.

The communication holes 341 are separately arranged at desired angular intervals in the sealing end portion 34. In the illustrated embodiment, an opening of each hole is in the form of a sector extending in an angular direction (see FIG. 10C).

In the present invention, the shape and structure of each communication hole 341 are not limited to the above-described ones and depending on the construction (the structure for the arrangement of the working medium passages) of the handle portion 2, the communication hole can have a desired shape such as a circular shape or a bossed construction.

FIG. 10A to FIG. 10C show a positioning projection on a front face of the sealing end portion 34 for guiding a portion to be bonded with the sealing end portion 24 of the handle portion 2.

The communication hole 32 formed inside the main body portion 31 of the coupling portion 3 is open at an end thereof so that the free end portion of the working medium conduit 4, namely, a working-medium-conduit-side coupling portion 4A is fitted and received therein (see FIG. 1).

In the communication hole 32, three hole sections are formed with their diameters increasing stepwise as viewed in a direction from the sealing end portion 34 to the engaging portion 33. These three hole sections are in communication with the air supply hole 3411, the air exhaust hole 3412 and the water supply hole 3413, respectively, in the sealing end portion 34 and further, with the respective working medium passages 41,42,43.

The engaging portion 33 which is maintained in engagement with the working medium conduit 4 of the coupling portion 3 is provided with an engaging annular groove 331 in the illustrated embodiment.

The engaging annular groove 331 makes up a portion detachably connectable with the working medium conduit 4. In the illustrated embodiment, the engaging annular groove 331 is formed in an outer peripheral portion of the engaging portion 33. An engaging portion (spring steel+engaging steel balls) of the working-medium-conduit-side coupling portion 4A (see FIG. 1) is in detachable engagement with the engaging annular groove 331. Owing to the construction of the above connecting portions, the coupling portion 3 and the working medium conduit 4 are rotatable relative to each other.

In the present invention, the structure of the connecting portion is not limited to the above-described structure and may be replaced by another structure known in the present field of art. Corresponding to this replacement, the specific structure of the engaging portion 33 is modified.

In the present invention, the coupling portion 3, for example, the coupling portion (3) made of the synthetic resin is produced by conducting integral molding in accordance with injection molding.

More specifically, the handle portion 2 made of the synthetic resin can be integrally molded by conducting injection molding in a mold while placing discrete cores at positions corresponding to the communication hole 32 communicable with the individual medium passages 41,42,43 of the working medium conduit 4 (see FIGS. 10A to 10C).

Needless to say, the handle portion 2 is not limited to the above-described integrally molded product and may be formed of a desired number of split members such as split members of a half-split structure. This is not limited to the coupling member 3 but is also applied to the other portions, that is, the head portion 1 and the handle portion 2.

In the present invention, the sealing end portion 34 of the handle portion 3 and the sealing end portion of the handle portion 2 are bonded together by a desired bonding method.

For example, integral bonding is achieved by adhesion, bonding, welding or the like.

In the illustrated first embodiment, the split members are integrally bonded together by ultrasonic welding.

Incidentally, both the members are provided at bonding portions thereof with positioning recesses 242 and the positioning projections 342 so that they correspond to each other.

In the illustrated embodiment, the positioning projections 342 are arranged on a side of the hand portion 3 whereas the positioning recesses 242 are arranged on a side of the handle portion 2. They can be swapped with each other.

Concerning the positions of the positioning recesses 242 and projections 342, assume, for example, that two positioning recesses and two projections are arranged at bonding portions. As the positions of the recesses 242 correspond to those of the projections 342, respectively, a description will be made only about the projections 342. Unless the projections 342 are arranged at an angular interval of 180°, in other words, in a mutually antipodal relationship, the working medium passages in the handle portion 2 can be registered with the working medium passages in the coupling portion 3 so that the former working medium passages can be joined and communicated with the latter working medium passages.

Referring next to FIG. 11, the odontotherapeutic hand piece according to the second embodiment of the present invention will next be described. The odontotherapeutic hand piece according to the second embodiment has the following characteristic features:

i) A head portion 1 is integrated in its entirety with a left-hand half-split member a2 of a handle portion 2. The left-hand half-split member a2 is integrally joined with a right-hand half-split member a1 into a final product, that is, the odontotherapeutic hand piece A.

ii) As the whole head portion 1 is formed as a single-piece member, a rotary member 11 accommodated in a head chamber is formed as a unit-type cartridge and is detachably mounted in the head portion 1.

iii) A cap 15 of the head portion 1 is constructed so that it can be detached upon mounting or dismounting the rotary member 11. Incidentally, the cap 15 is constructed to function as a fixing member for the rotary member 11.

The construction other than those mentioned above and the operation are similar to those of the first embodiment.

With reference to FIG. 12, the odontotherapeutic hand piece A according to the third embodiment of the present invention will next be described.

The odontotherapeutic hand piece according to the third embodiment is characterized in that three parts, namely, a head portion 1, a handle portion 2 and a coupling portion 3 are constructed by a pair of left-hand and right-hand, half-split members a1,a2.

The construction other than those mentioned above and the operation are similar to those of the first embodiment.

Figure 13:
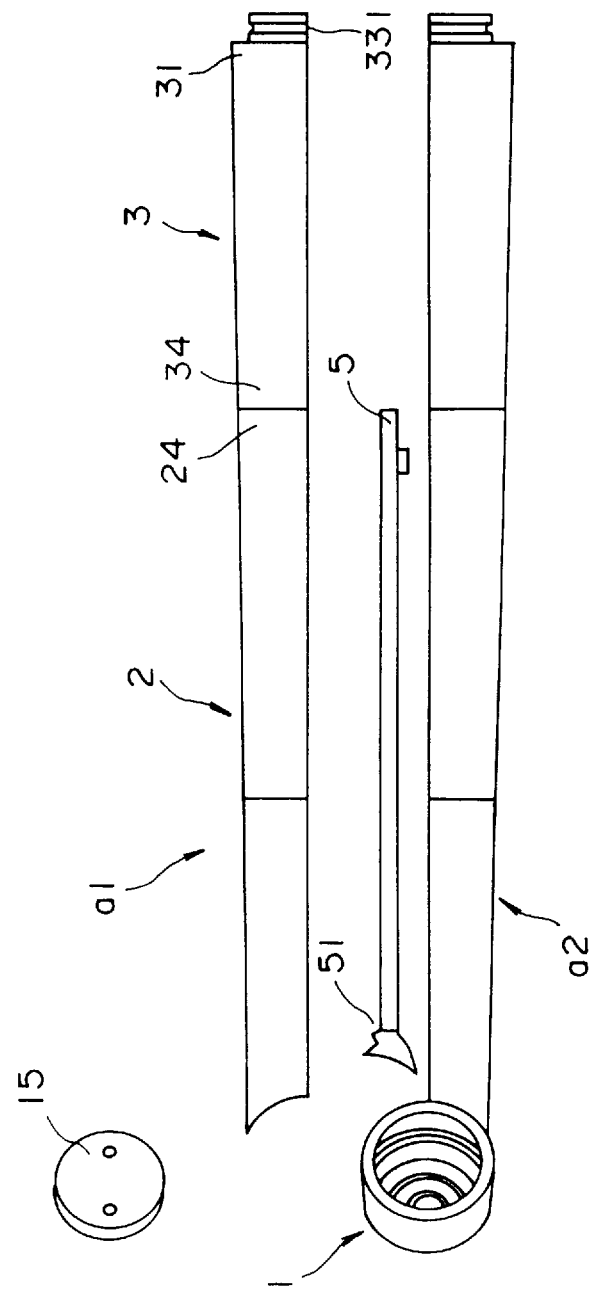
FIG. 13 is a plan view of split members which make up an odontotherapeutic hand piece according to a fourth embodiment of the present invention.

Referring next to FIG. 13, the odontotherapeutic hand piece according to the fourth embodiment of the present invention will be described.

The odontotherapeutic hand piece A according to the fourth embodiment has the following characteristic features:

i) Two parts, namely, a handle portion 2 and a coupling portion 3 are constructed of a pair of left-hand and right-hand, half-split members a1,a2.

ii) A head portion 1 is integrated in its entirety with one (a2) of the half-split members.

The construction other than those mentioned above and the operation are similar to those of the first embodiment.

Figure 14:
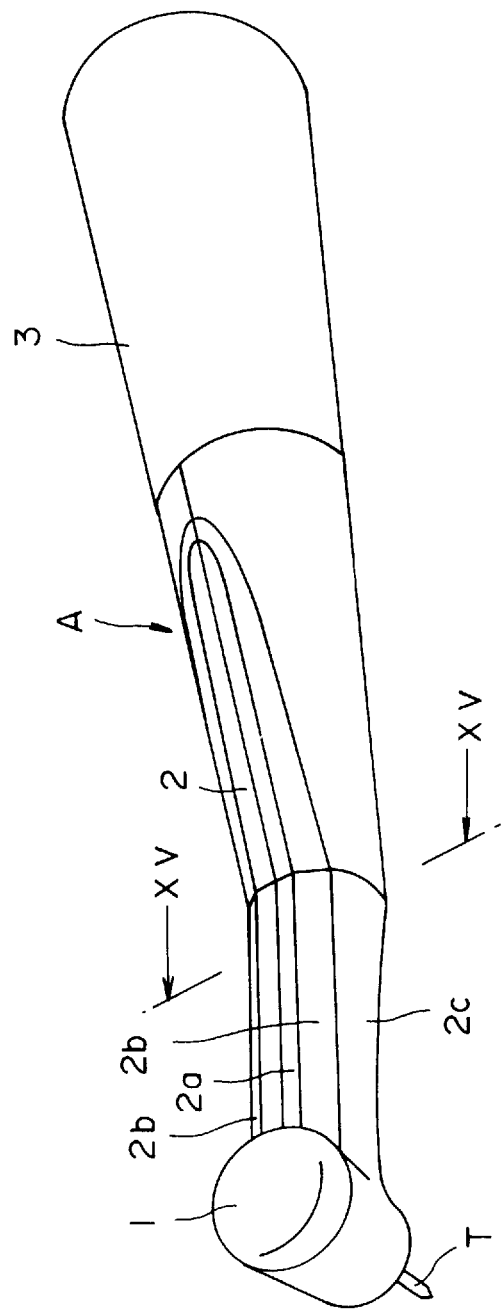
FIG. 14 is a perspective view illustrating outer configurations of an odontotherapeutic hand piece according to a fifth embodiment of the present invention.
Figure 15:
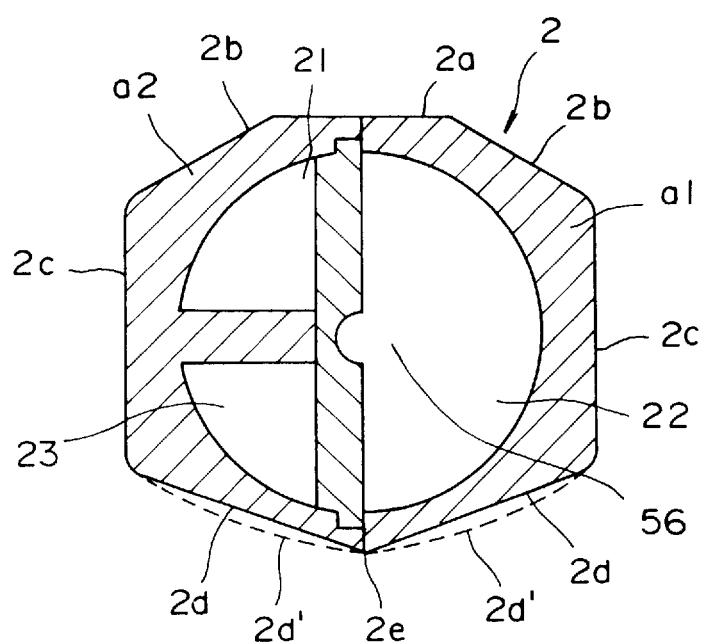
FIG. 15 is a cross-sectional view taken in the directions of arrows XV—XV of FIG. 14.

Referring finally to FIG. 14 to FIG. 15, the odontotherapeutic hand piece according to the fifth embodiment of the present invention will be described.

A characteristic feature of the odontotherapeutic hand piece according to the fifth embodiment resides in that the external configuration of the hand piece has been improved to make the handling of the hand piece easier, especially to permit accurate operation or handling of the hand piece relative to a diseased surface or part under treatment.

Namely, the external configuration or structure of a handle portion 2 is formed of a top wall portion 2a in the form of a horizontal wall, a tilted left wall portion 2b and a right wall portion 2b extending from opposite sides of the top wall portion 2a, a left side wall portion 2b and a right side wall portion 2c extending in the form of hull-shaped curved wall portions from said tilted left and right wall portions 2b,2c, and a bottom wall portion 2e. The curved wall of the bottom portion 2e may be of a configuration indicated by a solid line 2d or of a configuration shown by a dashed line 2d'.

This external configuration provides the handle portion 2 with improved gripping property and using one or more of the individual wall portions as reference(s) (for example, using the angles of inclination of the individual wall portions relative to a horizontal direction), the hand piece can be accurately operated or handled.

What is claimed is:

1. An odontotherapeutic hand piece formed of a head portion, in which a rotary member provided with turbine blades is accommodated, a handle portion connected to said head portion and a coupling portion arranged in continuation with said handle portion, said odontotherapeutic hand piece having a working medium conduit arranged in an internal space of said coupling portion and detachably engaged with said coupling portion for supplying a working medium to said odontotherapeutic hand piece, wherein:

said head portion, said handle portion and said coupling portion are made of a material which permits integral molding;

said head portion, said handle portion and said coupling portion are integrally joined together;

said head portion, said handle portion and said coupling portion are formed of plural split members molded of a material which permits integral molding, and said split members are integrally joined together; and said handle portion is formed of a pair of left-hand and right-hand half-split members, one of said paired left-hand and right-hand half split members is formed of a split member having a portion of said head portion integrally molded therewith, said handle portion having a shielding plate between said paired left-hand and right-hand half-split members, and said paired left-hand and right-hand half-split members are integrally joined together at joining surfaces thereof.

2. An odontotherapeutic hand piece according to claim 1, wherein said joining surfaces of said paired left-hand and right-hand half-split members are coplanar with a rotary shaft of said rotary member accommodated in said head portion.

3. An odontotherapeutic hand piece according to any one of claims 1 to 2, wherein:

(i) said paired left-hand and right-hand half-split members corresponding to said handle portion are formed of gutter-like members having a substantially semicircular cross-section;

(ii) one of said paired left-hand and right-hand half-split members is provided with a rib extending out from an inner peripheral wall thereof and extending in a direction of a longitudinal axis thereof; and (iii) said rib is in contact with one side of said shielding plate when said left-hand and right-hand half-split members and said shielding plates are joined together.

4. An odontotherapeutic hand piece according to claim 3, wherein when said paired left-hand and right-hand split members have been integrally joined together, an upper space and a lower space divided by said rib in said one split member form an air supply passage and a water supply passage, respectively, and said the other split member forms an air exhaust passage.

5. An odontotherapeutic hand piece according to claim 3, wherein said joining surfaces of said paired left-hand and right-hand split members are provided with positioning concavities and positioning convexities, respectively, for mutual joining.

6. An odontotherapeutic hand piece according to claim 1, wherein said material permitting integral molding is an injection-moldable synthetic resin having a glass transition potion of at least 100° C.

7. An odontotherapeutic hand piece according to claim 1, wherein said material permitting integral molding is a die-casting aluminum alloy.

8. An odontotherapeutic hand piece formed of a head portion, in which a rotary member provided with turbine blades is accommodated, a handle portion connected to said head portion and a coupling portion arranged in continuation with said handle portion, said odontotherapeutic hand piece having a working medium conduit arranged in an internal space of said coupling portion and detachably engaged with said coupling portion for supplying a working medium to said odontotherapeutic hand piece, wherein:

said head portion, said handle portion and said coupling portion are made of a material which permits integral molding;

said head portion, said handle portion and said coupling portion are integrally joined together; and said handle portion and said coupling portion are provided with sealing end portions at end-face joining portions thereof, and said sealing end portions define light-guide holding portions for holding a light guide along a central axis of said handle portions and openings communicating with a working medium passage.

9. An odontotherapeutic hand piece according to claim 8, wherein one of said end-face joining portions is provided with at least one positioning concavity and the other end-face joining portion is provided with a like number of positioning convexity for mutual joining.

10. An odontotherapeutic hand piece according to claim 9, wherein plural positioning concavities and a like number of positioning convexities are arranged so that any two of said positioning concavities and corresponding two of said positioning convexities are not located in a mutually antipodal relationship with respect to central axes of said handle portion and said coupling portion.

11. An odontotherapeutic hand piece formed of a head portion, in which a rotary member provided with turbine blades is accommodated, a handle portion connected to said head portion and a coupling portion arranged in continuation with said handle portion, said odontotherapeutic hand piece having a working medium conduit arranged in an internal space of said coupling portion and detachably engaged with said coupling portion for supplying a working medium to said odontotherapeutic hand piece, wherein:

said head portion, said handle portion and said coupling portion are made of a material which permits integral molding;

said head portion, said handle portion and said coupling portion are integrally joined together; and said coupling portion is formed of an engaging portion engageable with an end portion of said working medium conduit, a main portion defining therein a communication hole communicated with a working medium passage of said working medium conduit, and a sealing end portion joined to said handle portion and having a communication hole communicated with said communication hole.

12. An odontotherapeutic hand piece according to claim 11, wherein said communication hole comprises three successive hole sections coaxially formed with diameters increasing stepwise as viewed in a direction from said sealing end portion toward said engaging portion of said coupling portion and said three hole sections are in communication with said communication hole in said sealing end portion.

13. An odontotherapeutic hand piece formed of a head portion, in which a rotary member provided with turbine blades is accommodated, a handle portion connected to said head portion and a coupling portion arranged in continuation with said handle portion, said odontotherapeutic hand piece having a working medium conduit arranged in an internal space of said coupling portion and detachably engaged with said coupling portion for supplying a working medium to said odontotherapeutic hand piece, wherein:

said head portion, said handle portion and said coupling portion are made of a material which permits integral molding;

said head portion, said handle portion and said coupling portion are integrally joined together; and said handle portion has an outer configurational structure which is composed of a top wall portion in the form of a horizontal wall, a tilted left wall portion and a right wall portion extending from opposite sides of said top wall portion, a left side wall portion and a right side wall portion extending in the form of hulls-shaped curved wall portions from said tilted left and right wall portions, and a bottom wall portion.

* * * * *